United States Patent [19]

Lenke et al.

[11] 3,997,613

[45] Dec. 14, 1976

[54] POLYACETAL AND POLYKETAL COMPOSITIONS

[75] Inventors: Gerd M. Lenke, Dover, Del.; Kent B. McReynolds, Telford, Pa.

[73] Assignee: Reichhold Chemicals, Inc., White Plains, N.Y.

[22] Filed: Dec. 6, 1974

[21] Appl. No.: 530,106

Related U.S. Application Data

[63] Continuation-in-part of Ser. No. 300,685, Oct. 25, 1972, abandoned.

[52] U.S. Cl. .................. 260/609 R; 260/30.8 R; 260/481 R; 260/761
[51] Int. Cl.$^2$ ........................... C07C 149/14
[58] Field of Search ...... 260/609 R, 30.8 R, 481 R, 260/761

[56] References Cited

UNITED STATES PATENTS

| | | | |
|---|---|---|---|
| 2,668,862 | 2/1954 | Price | 260/609 R |
| 2,905,720 | 9/1959 | Benneville et al. | 260/609 R |
| 2,905,721 | 9/1959 | Benneville et al. | 260/609 R |
| 3,003,853 | 10/1961 | Wilgus et al. | 260/609 R |
| 3,290,382 | 12/1966 | Hubscher | 260/609 R |
| 3,446,775 | 5/1969 | Bertozzi | 260/609 R |
| 3,503,930 | 3/1970 | Morris et al. | 260/609 R |
| 3,635,736 | 1/1972 | Oftedahl | 260/609 R |

OTHER PUBLICATIONS

Lienhard et al., J. Am. Chem. Soc. 88 pp. 3982–3995 (1966).
Walker; "Formaldehyde" (1963) pp. 279–280.

*Primary Examiner*—Lewis Gotts
*Assistant Examiner*—D. R. Phillips

[57] ABSTRACT

Water-insoluble compositions having substantial antioxidant activity which may be used as plasticizers are produced by liquid phase reaction of (a) dimercaptans or mercapto alcohols or combination of these with diols or polyols, (b) aldehydes and/or ketones, and (c) monomercaptans and/or mono-alcohols in the presence of an acid catalyst.

15 Claims, No Drawings

POLYACETAL AND POLYKETAL COMPOSITIONS

CROSS-REFERENCE TO RELATED APPLICATIONS

This application is a continuation-in-part of application Ser. No. 300,685 entitled "Novel Plasticizer Compositions and Method for Their Preparation," filed Oct. 25, 1972, now abandoned.

BACKGROUND OF THE INVENTION

This invention relates to new compositions of matter which may be useful as plasticizers for polymeric materials. More particularly, the invention relates to a novel class of polymers which are capable of plasticizing a wide variety of both natural and synthetic polymers.

Plasticizers are an important adjunct to the utilization of polymeric materials in that they are widely incorporated in both natural and synthetic polymers to increase the workability, flexibility or distensibility of such materials. In addition, they are often used as extenders for polymeric materials. In the plasticization or extension of organic polymers, organic plasticizers are generally used which are usually moderately high molecular weight liquids or, occasionally, low-melting solids.

Though there is considerable debate as to the mechanism by which various plasticizers function. Most plasticizers for polymeric materials are of the solvent type, i.e. rather high boiling, normally liquid organic compounds which are chemically inert toward the polymers in which they are used, but in which the polymer swells or is at least partially soluble and will therefore be readily softened by intimate contact with the plasticizer. The most widely used solvent-type plasticizers include esters of carboxylic acids or phosphoric acid, hydrocarbons, halogenated hydrocarbons, ethers, glycols and sulfonamides.

In the selection of a plasticizer, it is of particular importance that the plasticizer exercise the effect for which it is intended without undue adverse effect on other properties of the polymeric material and that it be at least comparable in cost and preferably lower in cost than the polymer to which it is added.

A particular problem in the field of polymer plasticization has been the plasticization of rubbers which are to be exposed to high temperatures under oxidative conditions. Plasticizers for this application must be non-volatile, must be compatible with the base polymer and must maintain the flexibility of the rubber and preferably have antioxidant activity, all of which must be done without significant impairment of the other performance properties of the rubber.

A new class of compositions has been discovered which not only have the above-described capability to plasticize high temperature performance rubber, but also to improve the resistance of such rubber to oxidative deterioration. Furthermore, these compositions, which possess the versatility to plasticize and otherwise improve the properties of many polymeric materials, have exceptional resistance to hydrolysis.

DISCUSSION OF THE PRIOR ART

In U.S. Pat. No. 2,785,947, Kress and Abrams disclose the use of polyacetals of monoaldehydes and dialdehydes containing up to 8 carbon atoms to treat fabrics and thus improve their laundry and dry cleaning durability. The disclosed polyacetals are water-soluble. Kress, in U.S. Pat. No. 2,785,949 discloses the use of polyacetals like those disclosed in 2,785,947 as substitutes for melamine resins to give dimensional stability to cellulosic textile materials. In U.S. Pat. No. 2,785,995 to Kress the same type of polymeric acetals are used to improve the wet strength of paper. Matuszak el al in U.S. Pat. No. 2,796,401 disclose the use of complex formals prepared by reacting formaldehyde, mono-alcohols and polyhydric alcohols as a lubricant base. The polyformals disclosed are water-soluble. In U.S. Pat. NO. 2,786,081 to Kress, the inventor discloses the use of water-soluble aldehyde/polyol condensation products as plasticizers "either of water-soluble or organic-soluble polymers." However, no example of such use is given. Cottle and Young, in U.S. Pat. No. 2,796,423, reveal the use of polyformals similar to those of U.S. Pat. No. 2,796,401 as synthetic lubricants. Mertzweiller, in U.S. Pat. No. 2,796,441, discloses the use of polyformals of formaldehyde and long chain monoalcohols derived from the Oxo process as synthetic lubricants. In U.S. Pat. No. 2,838,573, Matuszak and Ready disclose the preparation of complex formal lubricants by reacting formals with a glycol. Johnson in U.S. Pat. No. 2,846,404 discloses the use of polyformals to inhibit foam in steam boilers. Kress again, in U.S. Pat. No. 2,878,294, discloses water-soluble polyacetals prepared by reacting polyalkylene glycol or thiodiglycol, monohydric alcohol and aldehydes, which products are said to be useful as hydraulic fluids.

The above described polyacetals of the prior art would not be operable as plasticizers for elastomers such as nitrile and chloroprene rubbers because they are substantially incompatible therewith. Moreover, they would not enhance the heat and oxidation resistance of polymers to which they were added since they contain no component or functional group capable of taking part in an anti-oxidative chemical reaction.

Thus, while the prior art teaches much about the composition and properties of water soluble polyacetals, the properties and various uses therefrom, there is no suggestion of the unique properties and uses of the compositions of the invention.

BRIEF DESCRIPTION OF THE INVENTION

The composition of the present invention which may be broadly characterized structurally as polyacetals and polyketals, is represented in general by the following chemical structure:

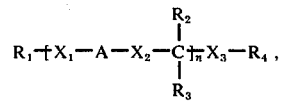

wherein $R_1$ is selected from the group consisting of hydrogen and a monovalent group

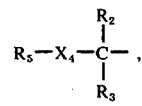

$R_2$ and $R_3$ are independently selected from the group consisting of hydrogen, perchlorocarbyl, chlorohydrocarbyl and hydrocarbyl with the hydrocarbyl moiety having from 1 to 30 carbon atoms, $R_4$ is hydrocarbyl having 1 to 30 carbon atoms or a monovalent residue selected from the group consisting of a dimercaptan, a monomercapto alcohol and a diol. $R_5$ is hydrocarbyl having from 1 to 30 carbon atoms, $X_1$, $X_2$, $X_3$ and $X_4$ being independently selected from the group consisting of sulfur and oxygen with at least 30 mole percent of sulfur present in the total selection, A is the divalent residue selected from the group consisting of a dimercaptan, a monomercapto alcohol and a diol, and n is an integer from 1 to 50.

Compounds of the above general formula, which are a unique class of polyacetals and polyketals, may be prepared by the liquid phase reaction of a primary chalcogen mono-alcohol and polyol, preferably dimercaptan, and an aldehyde or ketone, with a chalcogen mono-alcohol, preferably a mercaptan, in the presence of an acid catalyst. On the other hand, when the reaction is conducted in the presence of the monomercaptan or mono-alcohol, at least a portion of the terminal hemiacetal or hemiketal groups undergo a condensation reaction with the monomercaptan or mono-alcohol by which the polymer is "endcapped" with the monomercaptan or mono-alcohol residue. Endcapping of this nature can be carried out simultaneously with or after formation of the polyacetal or polyketal structure.

DEFINITIONS

Within the context of the invention, various terms used herein have the following special meanings:

Chalcogen has been used to denote the elements sulfur and/or oxygen only;

Mono-alcohol residue refers to the monovalent moiety which would result from exclusion of the hydroxy or mercapto group from a chalcogen mono-alcohol. The term does not imply nor is it limited to any particular reaction mechanism.

Hydrocarbyl refers to the following hydrocarbon radicals:
alkyls
alkenyls
alkynyls
aryls
arylalkyls (aralkyls)
arkylaryls (alkaryls)

Protonic acid denotes acids which, in an appropriate solvent, such as water, having a high dielectric constant are capable of dissociation into a proton and an anion and which have a Dissociation Constant of at least $1 \times 10^{-5}$ and preferably at least $1 \times 10^{-2}$ (measured in water).

Perchlorocarbyl denotes hydrocarbyl residues in which all of the hydrogens are replaced by chlorine, such as in trichloromethyl, pentachloroethyl, and the like.

Chlorohydrocarbyl refers to hydrocarbyl residues in which a portion of the hydrogens are replaced by chlorine, such as monochloromethyl, dichloromethyl, monochloroethyl, and the like.

COMPONENTS OF THE REACTION

The following are exemplary of reactants which may be used to form the compositions of the invention:

Examples of the dimercaptans (building blocks of the composition) are:

dimercapto propylether (1,7-dimercapto-4-oxaheptane)
1,4-dimercapto butane
1,5-dimercaptopentane
1,6-dimercaptohexane
1,5-dimercapto-3-oxapentane (dimercapto-diethylether)
$HS-CH_2-CH_2+O-CH_2-CH_2)_n SH$    n = 2 to 10
1,5-dimercapto-3-thiapentane
$HS-CH_2-CH_2+S-CH_2-CH_2)_n SH$    n = 2 to 15
1,7-dimercapto-3,5-dioxaheptane
1,7-dimercapto-3,5-dithiaheptane
1,4-(bis-methylene mercapto)-cyclohexane
1,4-(bis-methylene mercapto)-benzene
1,2-dimercaptoethane
1,3-dimercaptopropane
2,9-paramenthane dithiol (dipentene dimercaptan)
glycol dimercaptoacetate:

$$HS-CH_2-\underset{\underset{O}{\|}}{C}-O-CH_2-CH_2-O-\underset{\underset{O}{\|}}{C}-CH_2-SH$$

dithioerythritol:

$$HS-CH_2-\underset{\underset{OH}{|}}{CH}-\underset{\underset{OH}{|}}{CH}-CH_2-SH$$

dithiothreitol:

$$HS-CH_2-\underset{\underset{OH}{|}}{CH}-\overset{\overset{OH}{|}}{CH}-CH_2-SH$$

Examples of the monomercapto alcohols are:
2-mercaptoethanol
3-mercaptopropanol
4-mercaptobutanol
5-mercapto-3-oxapentanol-1

It is preferred to employ dimercaptans in synthesizing the compositions of the invention. Especially preferred are the primary dimercaptans with chain length of at least 4 carbon atoms and optionally at least one oxygen or sulfur atom.

Optionally, diols or polyols may be used in combination with dimercaptans and monomercapto alcohols. The amount of diols or polyols should not exceed 50 percent by weight of the dimercaptans and 25 percent by weight of monomercapto alcohols. The total concentration of sulfur in the finished product should preferably be at least 10 percent by weight and more preferably greater than 20 percent by weight.

Examples of the diols and polyols are:

2,2'-thiodiethanol (thiodiglycol)
$HO-CH_2-CH_2-S-CH_2-CH_2+O-CH_2-CH_2)_n OH$,  n = 1–5
(ethoxylated thiodiglycol)
$HO+CH_2-CH_2-O)_m CH_2-CH_2-S-CH_2-CH_2+O-CH_2-CH_2)_n OH$,
(ethoxylated thiodiglycol) m or n = 1–5

$$HO-CH_2-CH_2-S-CH_2-CH_2-O-\overset{\overset{CH_3}{|}}{CH}-CH_2-OH$$
(adduct of propylene oxide and thiodiglycol)

$$HO-CH_2-\overset{\overset{CH_3}{|}}{CH}-O-CH_2-CH_2-S-CH_2-CH_2-O-\overset{\overset{CH_3}{|}}{CH}-CH_2-OH$$

-continued (bis-propylene oxide adduct of thiodiglycol)
HO—CH$_2$—CH$_2$—S—CH$_2$—CH$_2$—(O—CH$_2$—CH$_2$—S—CH$_2$—CH$_2$)$_n$—OH,  n = 1–5
(thiodiglycol polyether)
HO—CH$_2$—CH$_2$—(S—CH$_2$—CH$_2$)$_n$—OH,  n = 2–6
(polyethylene sulfide diol)
HO—(CH$_2$)$_n$—S—(CH$_2$)$_m$—OH,  n = 2–4, m = 3–10
(monothiadiol alkylenes)
HO—CH$_2$—CH$_2$—S—CH$_2$—S—CH$_2$—CH$_2$—OH
(3,5-dithiaheptadiol-1,7)
HO—CH$_2$—CH$_2$—S—CH$_2$—CH$_2$—S—CH$_2$—S—CH$_2$—CH$_2$—S—CH$_2$—CH$_2$—OH
(3,6,8,11-tetrathiatridecadiol-1,13)
HO—CH$_2$—CH$_2$—S—CH$_2$—CH$_2$—O—CH$_2$—O—CH$_2$—CH$_2$—S—CH$_2$—CH$_2$—OH
(3,11-dithia-6,8-dioxa-tridecadiol-1,13)

$$HO-CH_2-CH_2-S-CH_2-\overset{\overset{O}{\|}}{C}-O-CH_2-CH_2-OH$$
5-hydroxy-3-thia-pentanoic acid mono-ethylene glycol ester
ethylene glycol (1,2-ethanediol)
poly(ethyleneoxide) glycols (e.g. diethyleneglycol, triethyleneglycol, etc.)
1,3-propanediol
1,2-propanediol
1,2,3-propanetriol (glycerol)
1-chloro-2,3-propanediol
1,4-butanediol
2-methyl-1,3 propanediol
1,5-pentanediol
3,3-dimethyl-1,3 propanediol (iso-pentandiol)
Pentaerythritol
1,6-hexanediol
2-ethyl-1,6-hexanediol
1,4-dimethylol-cyclohexane

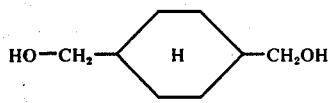

1,4-dimethylol-benzene

2-ethylhexanediol-1,3

The aldehydes and ketones which may be reacted with the chalcogen diols to form the polyacetal and polyketal compositions of the invention include the following:

| Aldehydes | Ketones |
| --- | --- |
| formaldehyde | acetone |
| paraformaldehyde | methyl-ethyl ketone |
| trioxane | cyclohexanone |
| acetaldehyde | 4,4-dimethyl-2-pentanone |
| propionaldehyde | acetophenone |
| butyraldehyde | dibenzyl ketone |
| benzaldehyde | 2-methylhexanone-5 |
| acrolein | methyl-(norbornyl-2-)-ketone |
| crotonaldehyde | 2-decanone |
| cinnamaldehyde | 3-ethyl-4-octanone |
| n-heptaldehyde | 6-undecanone |
| 2-methylpentanal | methyl-n-amylketone |
| n-octanal | methyl-iso-amylketone |
| 2-ethyl-2-hexanal | |
| n-nonal | |
| trichloroacetaldehyde (chloral) | |

In order to minimize loss of the carbonyl reactant and facilitate control over the reaction of the chalcogen polyol with the hydrocarbyl carbonyl compound, it is preferred in the synthesis of the product of the invention to employ carbonyl compounds which are substantially non-volatile up to the boiling point of water or which are present during the reaction in a substantially non-volatile intermediate form. For this reason, inter alia, it is preferred to use formaldehyde as the carbonyl compound since it rapidly reacts with the mercapto or hydroxy groups of the chalcogen mono-alcohol or polyol to form non-volatile hemiformal compounds which then condense further to formal linked polymers. Water is produced in this reaction which could bind any free unconverted aldehyde to a non-volatile hydrate. Likewise, it is preferred to use paraformaldehyde as a source of formaldehyde since it is relatively non-volatile but depolymerizes readily under reaction conditions. The free aldehyde is almost instantly used up in the formation of hemiformal.

Preferred monothiols which may be used to produce the hydrocarbyl terminated polyacetals and polyketals of the invention have the general configuration R—SH in which R is a hydrocarbyl group containing from 4 to 30 carbon atoms. Preferred are primary mercaptans with alkyl groups containing 8 to 20 carbon atoms. Alkyl esters of thioglycolic acid may be used as well. Included among such suitable reactants are the following:
n-butyl mercaptan
iso-butyl mercaptan
n-octyl mercaptan
2-ethyl-hexyl mercaptan
n-dodecyl mercaptan
mixed $C_{12-13}$ primary mercaptans
hexadecyl mercaptan iso-octyl thioglycolate
cyclohexyl mercaptan
mixed primary tridecyl mercaptans*
n-nonyl mercaptan
benzyl mercaptan
p-chlorobenzyl mercaptan
dodecyl benzyl mercaptan
dodecyl thioglycolate
tridecyl-3-mercapto propionate

*Pennwalt Corp.

Mono-alcohols which may be used to endcap the hemiacetal- and hemiketal-terminated polyacetals and polyketals of the invention may include the following:

1-butanol
1-pentanol
benzyl alcohol
n-butylglycol
isobutyl glycol
n-butyl diglycol
isobutyl diglycol
n-butyl polyglycol
$C_4H_9$—$(O$—$CH_2$—$CH_2)$—$_nOH$, $n = 3$ to $10$
1-hexanol
1-heptanol
1-octanol
2-ethyl-hexanol-1
2-ethyl isohexanol
1-decanol
n-dodecanol-1
Neodol-23* (mixed $C_{12}/C_{13}$ primary alcohols)
Neodol-25 (mixed $C_{12}$–$C_{15}$ primary alcohols)
Neodol-45 (mixed $C_{14}/C_{15}$ primary alcohols
ethyleneglycol monobutyrate
ethyleneglycol monolaurate
ethyleneglycol monostearate
allyl alcohol
crotonic alcohol
ethylthioethanol (3 thiapentanol)

*Tradename of Shell Chemical Co., Houston, Texas.

From the foregoing discussion of the chalcogen monoalcohols and polyols which may be used in the invention, it will be apparent that the reactivity of the mercaptan and hydroxy groups thereof is the essential criterion of their suitability for synthesis of the compounds of the invention. It will be recognized that the residues of the monomercaptans, mono-alcohols, dimercaptans, mercapto-alcohols, and polyols, as defined hereinabove, are capable of quite wide variations in structure, so long as the residual moiety does not interfere too greatly with the basic interactions of the mercaptan and hydroxy groups and/or the catalyst. Thus, the selection of particular chalcogen mono-alcohols and polyols may be used as a means of "tailoring" the molecule for use in a given polymer matrix. By selecting chalcogen mono-alcohols and diols as to size (molecular weight), configuration and polarity, the products of the invention can be varied widely in compatibility, efficiency, permanence and solvent power for particular polymers.

Thus, the above-referred chalcogen alcohol and polyol residues may be of either acyclic or cyclic configuration as well as combinations thereof and include hetero atoms such as sulfur, nitrogen and oxygen and substituent groups such as halogen, carboxyl groups and, in the case of the polyols, hydroxy groups. The chalcogen mono-alcohol and the polyol residues therefore include both substituted and unsubstituted alkyl, thiaakyl, oxa-alkyl, alkaryl, aralkyl, alkenyl, aryl, heterocyclyl, heterocycloalkyl, carboxyalkyl and poly-(alkyleneoxide) groups. Amine substituents, however, should be avoided.

Acids which may be used to catalyze the reaction of the chalcogen diols with the carbonyl compounds (aldehydes and/or ketones) include protonic acids, such as hydrochloric acid, sulfuric acid, hydrobromic acid, chlorosulfonic acid, phosphoric acid, methane sulfonic acid, p-toluene-sulfonic acid, dodecyl benzene sulfonic acid and other strong organic acids, such as trichloroacetic and trifluoroacetic acids. Lewis acids such as $CaCl_2$, $AlCl_3$, $BF_3$ and $BF_3$ etherate may also be used to catalyze the reaction, since they are rendered protonic in the presence of the alcohol reactants or even small amounts of water in the reaction system, such as would result from the condensation reactions or might be present as an impurity in the starting materials. Strong organic acids, such as p-toluene sulfonic acid, dodecylbenzene sulfonic acid, methane sulfonic acid, trichloroacetic acid and trifluoroacetic acid, are preferred catalysts for the above-described reactions because of their solubility in both the aqueous and organic phases of the initial reaction mixture.

DESCRIPTION OF THE PROCESS

One advantage of the compositions of the invention is that they are quite easy to synthesize and require only basic production equipment and moderate conditions of reaction pressure and temperature.

Basically, the method of synthesis is a single-step process in which all of the reaction components and the catalyst are charged at the start of the reaction. However, in some instances it may be advantageous to introduce certain components during a later stage of the reaction. The process may be conducted batch-wise or in a continuous operation.

The process is carried out as a bulk liquid phase reaction, in which at least one of the reactants is a liquid and is capable of acting as a dispersing medium for the other reactants. Thus, while any of the reactants, may be normally solids, they nevertheless must be dispersible in the liquid reactant medium and be reactive when so dispersed. Consequently, the reactants useful in the practice of the invention must be dispersible in the reaction mixture in at least one of the following ways: (1) solubility in at least one other reactant which is liquid; (2) non-solution dispersibility in at least one other reactant which is liquid; (3) solvency for at least one other reactant; and (4) constitution as a liquid phase in which at least one insoluble reactant is dispersible.

In most instances, the chalcogen polyols and monoalcohols are liquid at reaction conditions and the other reactants — whether liquids or solids — are soluble therein. One notable exception is paraformaldehyde which is insoluble in the reaction system, but upon dispersion therein is depolymerized by the presence of the catalyst to formaldehyde gas, which almost instantly takes part in the formation of a hemiformal, as discussed hereinabove. Another exception is the use of certain Lewis acid catalysts, such as calcium chloride, which are mainly insoluble in the other reactants, but are nevertheless dispersible therein.

The process is not particularly sensitive to reaction conditions and requires only modest heating to about 60° C to obtain adequate reaction rates. However, temperatures of at least about 90° C are preferred further to speed the reaction and also to facilitate separation of water formed during the reaction. Since water is formed by reaction of the carbonyl compound with the chalcogen poly- and mono-alcohol to form acetal or ketal linkages, it is preferred to remove the water by stripping in order to shift the equilibrium of the reaction to favor acetal or ketal formation. One molecule of water is formed for each acetal or ketal bond. So far as it is known the maximum reaction temperature is limited only by the volatility and/or thermal stability of the reactants and products therefrom, whichever may be controlling.

The synthesis of this new class of compounds is likewise not sensitive to pressure variations. It may be conducted at atmospheric pressure. However, higher than atmospheric pressure may in some instances be preferred to suppress volatilization of the reaction components. While vacuum conditions are permissible, vacuum will ordinarily not be preferred, except to facilitate the separation of water from the system during the final stage of the reaction.

It is preferred to carry out the process under inert atmosphere, such as nitrogen or inert gas (essentially $N_2$ and $CO_2$). The absence of oxygen during the reaction is desirable as to prevent the oxidation of free mercaptan groups and because of general safety considerations.

The end product of the reaction is comprised of a complex mixture of polyacetals or polyketals, as the case may be, conforming to the above-discussed general structural formula. Normally the stripped product will be homogeneous.

Water absorbing materials may also be used to remove reaction water from the product, e.g. $CaCl_2$, $CaSO_4$, $Al_2(SO_4)_3$, $Na_2SO_4$, $MgCl_2$, $MgSO_4$, $NaCl$, $KCl$, silica gel, molecular sieves and the like. In addition, hydrocarbon solvents may be admixed with the reaction mixture to form azeotropic mixtures with the reaction water, by which removal of the water by distillation can be facilitated. Examples of such solvents are benzene, toluene and xylene. These azeotroping agents may also serve as diluents in the case the invention product is soluble therein.

In some instances, it may be preferred to neutralize and/or remove the acidic catalyst residues upon completion of synthesis. This may be accomplished readily by means of the addition of an acid acceptor or preferably, a base. Suitable bases include NaOH, KOH, $Na_2CO_3$, $NaHCO_3$ and $K_2CO_3$ in powder, flake or pelletized form. Acid acceptors include molecular sieves, ion exchange resins, silicate polymers, aluminum oxides and the like.

Although it is contemplated that the products of the invention will have great utility for the plasticization of nitrile and polychloroprene rubbers, it will, of course, be realized that they are also effective for plasticizing and/or extending other hydrocarbon polymers, such as SBR, polybutadiene, polyisoprene natural rubber, polystyrene, and many other natural and synthetic hydrocarbon polymers. It appears that only specified variations of the products of this invention are suited for the plasticiation of substantially saturated all-hydrocarbon polymers, such as poly-$\alpha$-olefins, e.g. polyethylene, polypropylene, poly-n-butene, polyisobutene and copolymers thereof, including such elastomers known as EPM and EPDM.

Polymers of organic monomers which also contain atoms other than hydrogen and carbon can be also effectively plasticized by the products of this invention. Exemplary of such monomers are carboxylic acids (acrylic, methacrylic, fumaric, maleic and itaconic acids), acrylic and methacrylic acid derivatives (acrylonitrile, methacrylonitrile, acrylamide, methacrylamide, N-methylolacrylamide), vinyl chloride, vinylidene chloride, vinyl esters (vinyl acetate), vinyl ethers, vinyl ketones, and vinyl heterocyclic compounds (N-vinyl pyrrolidone and vinyl pyridines).

In the formulation of polymers utilizing the plasticizers of the invention, the amount of plasticizer relative to the polymer can be varied over a wide range, depending, of course, upon (1) the character of the particular plasticizer, (2) the character of the polymer; (3) the type of modification which is sought for the polymer; and (4) the extent of polymer modification which is sought.

In the case of polymers with a relatively low polarity, such as most $\alpha$-olefin and diene rubbers, the hydroxy content of the plasticizers should be below about 1 meq. OH/g (determined by the Acetic Anhydride Method of C. L. Ogg, W. L. Porter, and C. O. Willits, Ind. Eng. Chem. Anal., Ed. 17, pp. 394–397 (1945)), and most preferably they should have a hydroxy content below about 0.2 meq. OH/g. At higher hydroxy contents, the plasticizers may not be sufficiently compatible and may effect premature curing of the green rubber stock. The number average molecular weight of the plasticizers used in most rubbers should typically be in the range from about 400 to about 2000 and preferably from about 500 to about 1500. The plasticizers may be present in amounts of from about 5 to about 50 and preferably from about 10 to about 30 parts per hundred rubber (phr).

Products of this invention with average molecular weights in excess of 1500 generally are useful for other than plasticizing applications, such as hydraulic fluids, lubricants, protective waxes, and the like. Some of the lower molecular weight versions of the polyacetals and -ketals may be utilized as antifoam agents, surfactants and antistatic agents.

Products of the invention with at least one free mercaptan end group per average molecule ($R_1 = H$ and $X_1 = S$ in the general formula) can be useful as chemically reactive compounds, which are capable of attachment to polymers with carbon-carbon unsaturation and thus becoming an intricate part of those polymers.

Products with two free mercapto end groups are useful building blocks for the synthesis of higher molecular weight polymers by a variety of reactions. They also can function as long chain crosslinking agents for carbon-carbon unsaturated polymers.

The invention will be better understood by reference to the following examples in which all proportions are expressed in parts by weight unless otherwise indicated:

In expressing the thiol (SH) and the hydroxy (OH) content of the present composition, it should be distinctly understood that the Acetic Anhydride Method of C. L. Ogg, W. L. Porter and C. O. Willits, Ind. Eng. Chem. Anal., Ed. 17, pp. 394–397 (1945) was followed since a number of methods for obtaining hydroxy content are known in the art and the numerical values will vary somewhat depending upon the exact method used.

EXAMPLE I

The synthesis of a tridecyl endcapped product of the invention by the condensation of a di- and a monomercaptan with paraformaldehyde according to the following reaction formula was carried out:

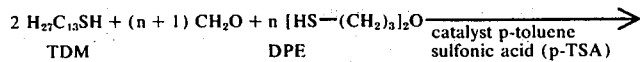

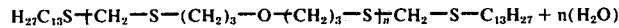

Procedure:

A 250 ml 3-necked round bottom flask, equipped with stirrer, reflux condenser, thermometer, gas in- and outlet, was purged with dry $N_2$ for about 45 minutes. Then the following reactants were charged into the flask:

4.15 g DPF (0.25 moles)
54 g TDM (0.25 moles)
0.3 g p-TSA

The liquid was stirred until all p-TSA was dissolved. Thereafter 11.5 g p-$CH_2O$ (0.38 moles) were added in small increments. The reaction was exothermic, as indicated by a temperature rise from 20° to 33° C. When the temperature fell to 31° C, a Dean Stark trap was installed between the flask and the reflux condenser and the reaction mixture was heated to 102° C. At this point condensation water was beginning to distill off. The temperature was further increased to 140° C, until approximately 6 ml of water collected in the Dean Stark trap. This indicated a substantially complete reaction (6.8 g $H_2O$ would be theoretically expected). As another indication of successful condensation, the viscosity of the liquid reaction mixture had increased notably.

The Dean Stark trap and condenser were replaced by a distillation bridge and a dry ice cooled receiving flask. The temperature was then lowered to 90° C and a moderate vacuum was applied to remove the residual volatiles. The reaction mixture was slowly heated to 150° C and then cooled down to 50° C, under vaccum. The apparatus was then filled up with dry $N_2$ and the remainder, a viscous, pale straw-colored liquid, was recovered. Although the starting materials had a strong mercaptan odor, the final product was nearly odorless. The yield was 104g (practically the theory). In the receiver another milliliter of condensation water was collected; thus, the total water also was in agreement with the theory.

The analysis for SH plus OH indicated less than 0.001 meq. SH and/or OH/g present in the product, which demonstrates a very complete reaction.

Samples of neoprene (polychloroprene) rubbers were prepared using the following compound recipe:

| a) Polychloroprene Rubber (Neoprene W*) | | |
|---|---|---|
| Curing agent (Maglite D - Merck) | 4.0 | |
| Antioxidant (Neozone D - phenyl-β-naphthyl-amine; duPont) | 20.0 | Parts by wt., basis 100 parts by wt. dry rubber |
| Reinforcing filler (20 SRF Black 80 Dixie Clay) | 100.0 | |
| Activator (ZnO) | 10.0 | |
| Promoter (stearic acid) | 0.5 | |
| Accelerator (NA-22 - 2-mercapto- | 1.0 | |

| -continued | |
|---|---|
| a) Polychloroprene Rubber (Neoprene W*) | |
| imidazoline; duPont) | |
| *Polychloroprene from duPont. | |

The samples also contained the following plasticizers:

| Sample A | 10 parts of tridecyl endcapped product of this example |
|---|---|
| Sample B | control (no plasticizer added) |
| Sample C | 10 parts Arizona 208* |
| Sample D | 10 parts rapeseed oil |

(*Plasticizer from Arizona Chemical - isooctyl ester of tall oil fatty acid)

The samples were compounded on a two-roll mill in a conventional manner.

Each of the above compounded rubbers was heated in an oven at 325° F until 100% cure was obtained as measured on a Monsanto Rheograph. Five samples each of the cured rubbers were then formed into Type C dumbbells and the tensile and elongation properties of each dumbbell was determined on a portion of each of the dumbbell samples. The remaining dumbbells were aged in an air-circulating oven for a period of time and at a temperature as set forth in the following tables, at the conclusion of which the cooled samples were likewise measured as to their tensile and elongation properties.

| Rheometer Data at 325° F (indicated scorchiness of compounds) | | | | |
|---|---|---|---|---|
| Sample | A | B | C | D |
| 1 point rise in seconds | 105 | 81 | 105 | 90 |

This indicates that use of the reaction product of this example and Arizona 208 contribute the least to the scorchiness of the final compounded chloroprene rubber.

All samples were vulcanized in 17.5 minutes at 325° F.

| Properties of Vulcanizates | | | | |
|---|---|---|---|---|
| Initial | A | B | C | D |
| Tensile Str. (psi) [1] | 2630 | 2640 | 2420 | 2430 |
| Modulus 100% (psi) [1] | 719 | 1024 | 670 | 710 |
| Modulus 200% (psi) [1] | 1026 | 1495 | 1004 | 990 |
| Elongation (max.) (%) [1] | 536 | 432 | 490 | 484 |
| Hardness [2] | 76 | 83 | 76 | 76 |
| Oven Aged 70 Hrs./250° F | | | | |
| Tensle Str. (psi) [1] | 2290 | 2270 | 1930 | 2190 |
| Modulus 100% (psi) [1] | 1000 | 1610 | 1230 | 1000 |
| Modulus 200% (psi) [1] | 1323 | 1880 | 1584 | 1350 |
| Elongation (%) [1] | 525 | 340 | 393 | 425 |
| Change Elong., (%) | −2 | −21 | −24 | −12 |
| Hardness [2] | 77 | 87 | 82 | 80 |

Properties of Vulcanizates

| Oven Aged 168 Hrs./250° F | | | | |
|---|---|---|---|---|
| Tensile Str. (psi) [1] | 1930 | 2240 | 2150 | 1760 |
| Elongation (%) [1] | 363 | 100 | 133 | 225 |
| Change Elong. (%) | −32 | −77 | −73 | −54 |
| Hardness [2] | 82 | 90 | 89 | 85 |
| Oven Aged 336 Hrs./212° F | | | | |
| Tensile Str. (psi) [1] | 2050 | 2160 | 2210 | 1850 |
| Elongation (%) [1] | 445 | 143 | 183 | 310 |
| Change Elongation (%) | −17 | −67 | −63 | −36 |
| Hardness [2] | 80 | 88 | 86 | 83 |
| Oven Aged 70 Hrs./275° F | | | | |
| Tensile Str. [1] | 1980 | 2200 | 1930 | 1900 |
| Elongation (%) [1] | 330 | 133 | 118 | 240 |
| Change Elongation (%) | −38 | −69 | −76 | −50 |
| Hardness | 81 | 88 | 87 | 81 |
| Plied Compression Set B | | | | |
| 70 Hrs./212° F [3] | 61 | 80 | 81 | 78 |
| Tear Resistance D-470 [4] | 66 | 40 | 50 | 52 |

[1] ASTM Test Procedure D-412-68
[2] ASTM Test Procedure D-2240-60
[3] ASTM Test Procedure D-395-69
[4] ASTM Test Procedure D-470-71

The above data demonstrate very clearly the advantage of the plasticizers of this invention as an additive in Neoprene, since the unaged properties of sample A are superior to all others in that it yields the highest elongation, while maintaining a high tensile strength at the same time. Heat aging under various conditions shows relatively small changes in elongation and demonstrates the clear superiority of sample A over all controls. Hardness and tensile strength are also maintained well. Compression set and tear resistance are both superior for Sample A.

Samples of nitrile rubbers were compounded using the following compound recipe:

b) Nitrile Rubber (Paracil BJLT*)

| | |
|---|---|
| Curing agent (spider sulfur) | 1.0 |
| Antioxidant (Plastonox 2246) [1] | 2.0 |
| Promotoer (ZnO) | 5.0 |
| Activator (stearic acid) | 0.5 |
| Accelerator (Monex) [2] | 0.6 |
| Filler (HiSil EP) [3] | 60.0 |
| Wax | 5.0 |
| TiO₂ | 10.0 |

Parts by wt., basis 100 parts by wt. dry rubber

*Medium high nitrile rubber from Uniroyal (33% acrylonitrile)
[1] 2,2-methylene bis (4-methyl-6-tert-butyl phenol); American Cyanamid.
[2] Tetramethylthiuram monosulfide; Uniroyal
[3] Silicon dioxide; PPG, Inc.

The samples also contained the following plasticizers:

Sample A  20 parts of tridecyl endcapped product of this example
Sample B  control (no plasticizer added)
Sample C  20 parts of dioctylphthalate (DOP)

The samples were compounded on a two-roll mill in a compounded manner.

Each of the above compounded rubbers was cured for 10 minutes at 325° F.

Properties of Vulcanizates

| Initial | A | B | C |
|---|---|---|---|
| Tensile Str. (psi) [1] | 1400 | 2240 | 1650 |
| Elongation (%) [1] | 810 | 780 | 880 |
| Hardness [2] | 55 | 72 | 64 |
| Oven Aged 70 Hrs./250° F | | | |
| Tensile Str. (psi) [1] | 1880 | 2740 | 2290 |
| Elongation (%) [1] | 515 | 338 | 433 |
| Hardness [2] | 61 | 79 | 70 |
| Oven Aged 70 Hrs./275° F | | | |
| Tensile Str. (psi) [1] | 1420 | 1020 | 1150 |
| Elongation (%) [1] | 80 | 32 | 50 |
| Hardness [2] | 77 | 88 | 86 |
| Ozone Resistance [3] | | | |
| Cracks at 100 pph O₃ After 120 hours | None | Cracked after 5 hours | None |

[1] ASTM Test Procedure D-412-68
[2] ASTM Test Procedure D-2240-60
[3] ASTM Test Procedure D-518-61

The above data indicate that the plasticizer of this invention as an additive in nitrile rubber is actually more effective in reducing the hardness of the vulcanizate than DOP and that the resistance to oven aging is significantly more improved, which is apparent from a higher final elongation and a lower hardness. Also, the ozone resistance of the vulcanizate A is much better than the unplasticized control.

EXAMPLE II

The synthesis of a tridecyl endcapped product of the invention by the condensation of a dimercaptan/diol/monomercaptan blend with formaldehyde was carried out using the following reaction materials:

83 g dimercaptopropylether (DPE)    (0.5 moles)
61 g thiodiglycol (TDG)    (0.5 moles)
45 g paraformaldehyde (p-CH₂O)    (1.5 moles)
108 g tridecylmercaptan (TDM)    (0.5 moles)

4 g para-toluene sulfonic acid (p-TSA)

A 0.5 liter reaction flask was used this time, otherwise the apparatus was the same as set forth in Example I.

TDH, p-CH$_2$O, and p-TSA were charged and dissolved by heating. Then DPE was added, which caused an upsurge in the temperature to 90° C. TDM was dropped from a dropping funnel into this mixture while maintaining the temperature of the mixture at 90°–105° C.

About 25 ml of H$_2$O were stripped off at atmospheric pressure (up to 140° C) and another 2 ml under vacuum at 90° to 140° C.

270 g of an amber, viscous liquid was obtained. The product contained only 0.1 meq. OH and/or SH/g, showing that the product is substantially completely reacted and endcapped with alkyl groups of the monomercaptan.

The product performed well as a plasticizer for Neoprene and nitrile rubbers.

EXAMPLE III

The synthesis of another product of the invention by the condensation of dimercaptan and monomercaptan with chloral as carbonyl component was carried out using the following reaction materials:

41.5 g dimercaptopropylether (DPE) (0.25 moles)
54.0 g tridecylmercaptan (TDM) (0.25 moles)
55.0 g trichloroacetaldehyde (Chloral) (0.375 moles)
0.5 g para-toluene sulfonic acid (p-TSA)

The general procedure set forth in Example I was employed.

A 250 ml reaction flask was charged with all chloral. DPE was dropped into the chloral from a dropping funnel within about 30 minutes, during which time the temperature increased from 23° to 70° C. Thereafter 0.5 g p-TSA was added and the mixture was heated to 90° C for half an hour.

TDM was dropped from a dropping funnel into the reaction mixture at about 80° to 90° C. Then 6 ml water were distilled off at atmospheric pressure, up to 150° C. Another 2 ml water were stripped under vacuum at 90° to 150° C.

A honey colored, viscous liquid product was obtained. It had 0.97 meq. SH or OH/g and contained 5.5% by weight chlorine.

The reaction product was useful as a plasticizing additive in polyvinylchloride and a butadiene-vinylidene chloride copolymer.

EXAMPLE IV

The synthesis of a product of this invention by the condensation of dimercaptopropylether (DPE) with acetophenone (ACP) as the carbonyl component was carried out in the presence of para-toluene sulfonic acid in accordance with the general procedure set forth in Example I.

Into a N$_2$ purged 250 ml reaction flask was placed 88g DPE (0.5 moles).

The liquid was stirred under a N$_2$ blanket and 54g of ACP were added and then 0.5g p-TSA. The mixture was heated to strip off condensation water.

At 180° to 198° C some water was forming and distilled off: 9 ml of water were collected (about the theoretical amount expected).

133g of a very dark tan, medium viscous, liquid product remained in the reaction flask. The IR spectrum of the product indicated that a considerable amount of ketone was converted to the polyketal; however, some residual carbonyl absorption was indicated.

The reaction product was found useful as a plasticizer in styrene-butadiene rubber. Oven cured it did not leach out with solvents and it did not evaporate during heat aging.

EXAMPLE V

The synthesis of a product of this invention by the condensation of dimercaptopropylether (DPE)/tridecylmercaptan (TDM) blend with methyl-iso-amylketone (MIAK) as the carbonyl component was carried out using the general procedure set forth in Example I.

A 1 liter reaction flask (N$_2$ purged) was used and all the following ingredients were charged at the start of the experiment:

166 g dimercaptopropylether (DPE) (1 mole)
152 g methyl-iso-amylketone (MIAK) (1.33 mole)
108 g tridecylmercaptan (TDM) (0.5 mole)
5 g dodecylbenzene sulfonic acid (BioSoft S-100*)

*Stepan Chemical Co.

There was a slight exotherm, when the BioSoft was added as the last ingredient (23°–33° C).

Under a N$_2$ blanket the liquid reaction mixture was heated to strip off condensation water. Starting at 137° C a distillate was collected of which the lower phase was mainly water and the top layer mainly MIAK. The stripping was continued until approximately 25 ml of water were collected (up to 197° C). Most of the higher distillate was recycled during the stripping; at the end of the reaction the final top layer (8 ml) of the distillate was discarded.

396g of a dark liquid product was obtained after stripping off the volatiles. The IR spectrum of the final product indicated that most of the ketone was converted to polyketal. From this and the fact that approximately the theoretical amount of condensation water was removed, it is concluded that the reaction was basically successful.

The reaction product was found useful as a plasticizer in Neoprene, polybutadiene and natural rubber and also as a hydraulic fluid.

EXAMPLE VI

This example demonstrates the synthesis of a dimercapto terminated polyformal by condensation of glycol dimercaptoacetate (GDMA) with formaldehyde in accordance with the following general reaction:

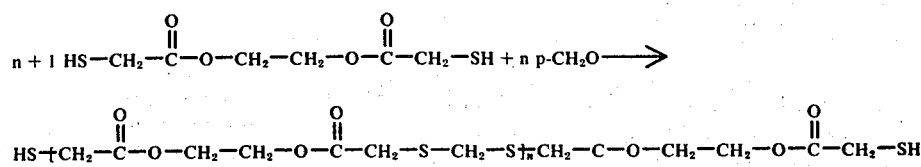

+ n H₂O

Procedure:

The apparatus used was the same as described in Example I. After thorough purging of the apparatus with dry N₂, the following reactants were charged into the reaction flask, in the sequence as shown:

149 g glycol dimercaptoacetate (GDMA*)   (0.71 moles)
80 ml benzene
20 g paraformaldehyde (p—CH₂O)   (0.57 moles)
1 ml dodecyl benzene sulfonic acid (Biosoft S-100 : Stepan chemical Co.)

*96.6% pure from Evans Chemetics

The benzene was employed as a diluent, as well as an azeotroping agent for the removal of reaction water during the condensation. BioSoft was used as catalyst. Immediately after the addition of BioSoft, an exothermic reaction set in, the temperature increased from 23° to 32° C within one hour. Thereafter, the temperature fell to 30° C and the reaction mixture was heated. At about 70° C all p—CH₂O had dissolved and a colorless, water-clear liquid resulted.

Most of the benzene (65 ml) was stripped off at atmospheric pressure at 80° to 120° C into a Dean Stark trap, together with 10 ml of reaction water. The remaining liquid was cooled to 90° C and the apparatus was converted to conduct a vacuum distillation of the residual volatiles. Under vacuum at 90° to 130° C an additional 2 ml water and 5 ml benzene were distilled off and collected in a dry ice cooled receiving flask. The fact that 12 ml water were distilled off the reaction mixture indicates virtual completeness of the condensation. Some of the benzene probably was lost into the vacuum line.

The remaining condensation product was cooled to room temperature under an N₂ atmosphere. It weighed 158g, which indicates a quantitative yield in agreement with theory. The product was a viscous, turbid and nearly colorless water insoluble liquid.

The free mercapto group concentration was 1.375 meq./g. This indicates an average molecular weight of 1450.

EXAMPLE VII

In this example a GDMA-polyformal was made in which one of the terminal mercaptan groups, per average molecule, is endcapped with a dodecyl radical by reaction with n-dodecyl mercaptan (DDM) in accordance with the following general reaction.

-continued 20 g paraformaldehyde (p-CH₂O)   (0.67 moles)
27 g dodecylmercaptan (DDM)   (0.13 moles)
1 ml methane sulfonic acid (MSA)

Right after the MSA was charged, an exothermic reaction started, raising the temperature from 25° to 40° C within 20 minutes. To complete the reaction, the mixture was heated to 92° C. The p-CH₂O dissolved during the heat-up and water started to form. The reaction temperature was slowly raised further to 148° C, to strip off the condensation water. After about 7 ml water were collected, a vacuum was applied and the removal of volatiles was completed at 92° to 148° C. A total of about 11 ml water was collected during the entire stripping, indicative of substantially complete condensation of all components.

The reaction product was a slightly amber, turbid liquid, which solidified over night to a soft wax. This wax could be remelted by heating with warm water. The product was not water soluble. The yield was 173g (98% of the theory).

The combined mercapto- and hydroxy groups concentration was determined by acetylation tests (see Example I) and found to be 1.05 meq./g. This suggests an average molecular weight of about 1000.

A high degree of alkyl termination can be attained by the use of monomercaptans as endcapping agents. The combination of monomercaptans with dimercaptans and formaldehyde is especially effective, as demonstrated in Example I. The high degree of endcapping with long chain alkyl groups aids the compatibility of the products of this invention in less polar rubbers and other polymers. This compatibility can be further enhanced by the use of ketones with bulky hydrocarbyl groups, as shown in Examples IV and V. By employing chloral as carbonyl component, as in Example III, the miscibility with chlorinated polymers, such as polyvinyl chloride and vinylidene chloride copolymers, is improved.

The use of dimercaptans in combination with monomercaptans not only assures a high degree of conversion to the desired endproducts, it also allows preparing compounds with a relatively high sulfur content. The high sulfur content is an important feature with respect to the antioxidant and antiozonant imparting properties of the compounds of this invention. Because of the high reactivity of the mercaptan groups towards the carbonyl compounds, polyacetals and polyketals can be more readily made from di- and monomercaptans than

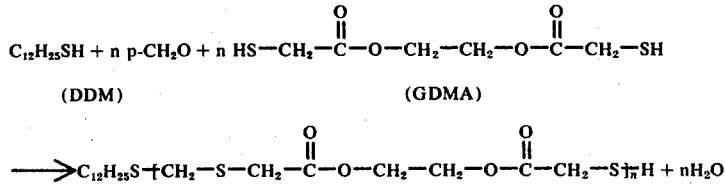

Procedure:

The apparatus was the same as in Examples I and VI. The procedure used was generally the same as in Example VI. The reactants below were charged in the sequence listed:

141 g glycol dimercaptoacetate (GDMA)   (0.67 moles)

by the use of corresponding diols and monoalcohols. For the same reason polyformals with rather high molecular weights can be made from dimercaptans and formaldehyde and, optionally, a small amount of a monomercaptan as chain terminator.

An interesting variation of this invention can be realized, when the polyacetals or polyketals have at least one free mercaptan endgroup per average molecule. If such a product is used as a plasticizer for a rubber, containing carbon-carbon unsaturation, the plasticizer can chemically attach itself to the rubber by addition of the free SH groups across the double bond of the rubber. The plasticizing function ordinarily is not impaired by this addition. However, the advantage gained is that the plasticizer has become an intricate part of the host polymer and thus can be neither extracted with solvents nor volatilized at elevated temperatures. Such an effect is demonstrated in Example IV.

What is claimed is:

1. A new water-insoluble polymeric composition having polythiaacetal-ketal linkages therein, of the formula:

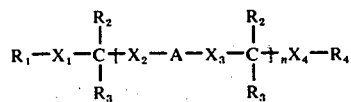

Wherein: $R_1$ and $R_4$ are independently selected from the group consisting of hydrogen and a monovalent residue of monomercaptans and monoalcohols, said monovalent residue that forms terminal groups being present in the statistical average polymer chain at least to about 50 mole percent of the terminal groups, and $R_1$ and $R_4$ are not both hydrogen in the statistical average polymer chain; $R_2$ and $R_3$ are independently selected from the group consisting of hydrogen and perchlorocarbyl and chlorohydrocarbyl radicals each having from 1 to 10 carbon atoms. $X_1$, $X_2$, $X_3$ and $X_4$ being independently selected from the group consisting of sulphur and oxygen with at least 30 mole percent of sulfur present in the total selection; A is the divalent residue of the compounds selected from the group consisting of dimercaptans, monomercapto alcohols and diols; and $n$ is an integer from 2 to 50; said monovalent residue selected from the group consisting of primary alkyl, thia-alkyl, oxa-alkyl, aralkyl, alkenyl and mixtures thereof; and said divalent residue selected from the group consisting of primary alkylene, thiaalkylene, oxa-alkylene, aralkylene, and mixtures thereof.

2. The composition of claim 1 in which the divalent residue is derived from a dimercaptan having from 4 to 20 carbon atoms.

3. The composition of claim 1 in which the divalent residue is derived from a monomercapto alcohol having from 4 to 20 carbon atoms.

4. The composition of claim 1 in which the divalent residue is derived from a diol having from 4 to 20 carbon atoms.

5. The composition of claim 1 in which the monovalent residue is derived from a monoalcohol having from 7 to 20 carbon atoms.

6. The composition of claim 1 in which the monovalent residue is derived from a monomercaptan having from 7 to 20 carbon atoms.

7. The composition of claim 1 in which is the liquid phase reaction product of a mercaptan, an aldehyde, and a diol.

8. The composition of claim 1 which is the liquid phase reaction product of a mercaptan, an aldehyde, and a dimercaptan.

9. The composition of claim 1 which is the liquid phase reaction product of a mercaptan, an aldehyde, and a monomercapto alcohol.

10. The composition of claim 1 which is the liquid phase reaction product of mercaptan, a ketone, and a diol.

11. The composition of claim 1 which is the liquid phase reaction product of mercaptan, a ketone, and a dimercaptan.

12. The composition of claim 1 which is the liquid phase reaction product of mercaptan, a ketone, and a monomercapto alcohol.

13. The composition of claim 7 in which the aldehyde is paraformaldehyde.

14. The composition of claim 10 in which the ketone is acetophenone.

15. The composition of claim 1 in which diol moiety in the polymer chain is not greater than 50% by weight of dimercaptan and 25% by weight of monomercapto alcohol.

* * * * *